(12) United States Patent
Teehan

(10) Patent No.: US 8,256,231 B2
(45) Date of Patent: Sep. 4, 2012

(54) CRYOSTAT

(75) Inventor: David Teehan, Warrington (GB)

(73) Assignee: Council for the Central Laboratory of the Research Councils, Warrington (GB)

( * ) Notice: Subject to any disclaimer, the term of this patent is extended or adjusted under 35 U.S.C. 154(b) by 1085 days.

(21) Appl. No.: 11/718,958

(22) PCT Filed: Nov. 8, 2005

(86) PCT No.: PCT/GB2005/004302
§ 371 (c)(1),
(2), (4) Date: May 9, 2007

(87) PCT Pub. No.: WO2006/051279
PCT Pub. Date: May 18, 2006

(65) Prior Publication Data
US 2007/0261429 A1 Nov. 15, 2007

(30) Foreign Application Priority Data
Nov. 9, 2004 (GB) .................................. 0424713.6

(51) Int. Cl.
*F25B 19/00* (2006.01)
*B23Q 3/18* (2006.01)
*B25B 1/22* (2006.01)
(52) U.S. Cl. .............................. 62/51.1; 269/61; 269/71
(58) Field of Classification Search .................. 62/51.1; 269/61, 71
See application file for complete search history.

(56) References Cited

U.S. PATENT DOCUMENTS
2,445,016 A * 7/1948 Bentley ........................ 269/59
(Continued)

FOREIGN PATENT DOCUMENTS
JP 61233343 10/1986

OTHER PUBLICATIONS
Anonymous: "Model HE-3-SOSV-S Cryostat" Product Brochure, [Online] Oct. 14, 2004, XP002367309 Retrieved from the Internet: URL:http://web.archive.org/web/20041014220343/http://www.janis.com/p-3he18.html> [retrieved on Feb. 9, 2006] the whole document.

(Continued)

*Primary Examiner* — Judy Swann
*Assistant Examiner* — Ian Soule
(74) *Attorney, Agent, or Firm* — Michael Best & Friedrich LLP

(57) ABSTRACT

A cryostat includes a rotatable mounting arranged to rotate about a first rotational axis, the mounting extending substantially in a first plane, a sample plate arranged in use to support a sample, located on the rotatable mounting, and a heat sink located adjacent the side of the mounting distant from the sample plate. A thermal conductor extends between the sample plate and the heat sink. The conductor extends through an aperture in the rotatable mounting. A rotatable sample holder for a cryostat includes a sample plate having a first side arranged in use to support a sample, a drive gear arranged to rotate about a first rotational axis, and a driven gear arranged to rotate about a second rotational axis, engaged with the drive gear and coupled to the sample plate such that rotation of the drive gear causes the driven gear and sample holder to rotate. The first rotational axis does not intersect the second rotational axis.

16 Claims, 5 Drawing Sheets

U.S. PATENT DOCUMENTS

| | | | | |
|---|---|---|---|---|
| 4,672,202 A | * | 6/1987 | Crossley et al. | 250/238 |
| 4,717,309 A | * | 1/1988 | Neuhaus | 414/735 |
| 4,751,828 A | * | 6/1988 | Coulter et al. | 62/51.1 |
| 4,754,249 A | * | 6/1988 | Yamamoto et al. | 335/216 |
| 4,770,435 A | * | 9/1988 | Cristie | 280/279 |
| 5,207,069 A | * | 5/1993 | Matsuda et al. | 62/55.5 |
| 5,249,425 A | * | 10/1993 | Longsworth | 62/6 |
| 5,611,207 A | * | 3/1997 | Hess | 62/51.1 |
| 5,613,367 A | * | 3/1997 | Chen | 62/47.1 |
| 5,828,280 A | * | 10/1998 | Spivey et al. | 335/216 |
| 6,094,923 A | * | 8/2000 | Rada | 62/51.1 |
| 6,725,673 B1 | | 4/2004 | Rada | |

OTHER PUBLICATIONS

International Search Report from the European Patent Office.

* cited by examiner

CRYOSTAT

CROSS-REFERENCE TO RELATED APPLICATIONS

This application is a United States national stage application filed under 35 U.S.C. §371 based upon international application no. PCT/GB2005/04302, filed Nov. 8, 2005, and published as WO 2006/051279 on May 18, 2006, which claims the benefit of and priority to United Kingdom Patent Application No. 0708780.2, filed Nov. 9, 2004, published as GB 2434954 A on Aug. 8, 2007, and issued as United Kingdom Patent GB 2434954 B on Dec. 2, 2009. The entire contents of each of the foregoing applications, publications, and patent are hereby incorporated by reference herein.

BACKGROUND

The present invention relates to cryostats, and in particular, to cryostat sample holder arrangements.

A cryostat is a vessel which allows a sample to be maintained at a very low temperature, for example, temperatures less than 0° C. The sample may then be subjected to experimentation in the cryostat at the very low temperature. The sample is placed on a sample holder or sample plate which is usually cooled to low temperatures by boiling a low temperature liquid into a gas, for example, by boiling liquid nitrogen at −196° C., or liquid helium at −269° C. In addition to cooling the sample, it is also often possible to manoeuvre the position of the sample in the cryostat by rotating the sample plate. This is desirable in spectroscopy experiments, as it allows the probing beam to remain static and the sample rotated, so as to alter the incident angle of the probing beam on the sample.

FIG. 1 shows a cross-sectional view of a known cryostat. A sample that is to be cooled is placed on to a sample plate in the cryostat, and is then subjected to cooling by boiling a low temperature liquid. The liquid is boiled in a gas tank, which is thermally coupled to the sample plate, by a thermal conductor. The conductor extends from the tank, around the outside of the sample plate movement apparatus, to the sample plate.

In the prior art cryostat shown, the sample plate and hence, sample, is rotated by means of a belt which extends around a pulley system, with a main drive shaft being mounted underneath the centre of the sample plate, i.e. directly on the rotational axis of the sample plate. However, such a drive arrangement has a number of disadvantages.

The use of a drive belt induces a slack into the system, such that it can be difficult to accurately control the rotational angle of the sample plate. Furthermore, the arrangement of the drive belt and the pulley system is relatively bulky, which means that a radiation shroud that is placed over the sample holder and sample has to be quite large in order to allow the equipment to be enclosed therein. In addition, the bulky equipment increases the amount of heat loss from the cryostat apparatus, such that it is not always possible to cool the sample to the very low temperatures that are often required in experiments.

In an attempt to address some of the above-mentioned problems inherent with using a pulley system to drive a cryostat sample holder, some manufacturers have replaced the pulley system with a bevel gear system, for example, a 'straight bevel', 'spiral bevel', or 'zerol bevel' gear system. Each of these types of bevel gear system consists of a rotating 'drive gear' or 'pinion', which is arranged to drive a 'driven gear' attached to one side of the sample holder. The axis of rotation of each gear is arranged such that it is along the radius of the other gear in the system. The axis of such bevel drive gears extends along the "zero line" of the driven gear, i.e. radial with respect to the driven gear. Hence, such bevel gear systems are referred to as "intersecting axis gears".

However, bevel gears tend to suffer from backlash. Backlash is the amount of "free play" in the gearing system. Bevel gears can also generally be driven backwards. This means that occasionally the drive gear and driven gear drive backwards due to torque acting on the driven gear. Hence, torque on the driven gear causes the driven gear to turn the drive gear itself, at least partially, and this decreases the accuracy with which the sample holder (and hence sample) can be rotationally positioned.

Other manufacturers have used rack and pinion gears, which suffer from similar problems.

SUMMARY

It is an aim of embodiments of the present invention to address one or more problems of the prior art, and to provide a sample holder for a cryostat that exhibits improved handling and/or cooling characteristics.

According to a first aspect of the present invention there is provided a cryostat comprising: a rotatable mounting arranged to rotate about a first rotational axis, the mounting extending substantially in a first plane; a sample plate arranged in use to support a sample, located on the rotatable mounting; a heat sink located adjacent the side of the mounting distant from the sample plate; and a thermal conductor extending between the sample plate and the heat sink, wherein the conductor extends through an aperture in the rotatable mounting.

Preferably, the thermal conductor comprises a flexible cable extending through the aperture.

Preferably, said cable comprises copper braid.

Preferably, the rotatable mounting is substantially annular, and the aperture extends substantially through the centre thereof.

Preferably, the conductor extends along said first rotational axis.

Preferably, the thermal conductor does not contact the rotatable mounting.

Preferably, the conductor is less than 5 cm in length.

Preferably, the cryostat comprises a temperature sensor comprising electrical wires, the electrical wires extending through the said aperture.

Preferably, at least one of the conductor and the temperature sensors is connected to the side of the sample plate adjacent the heat sink.

Preferably, the cryostat further comprises a hollow bearing extending around said first rotational axis, the conductor extending through the bearing, and the bearing supporting the rotatable mounting.

Preferably, the cryostat further comprises a drive gear arranged to rotate about a second rotational axis, the rotatable mounting comprising a driven gear arranged to rotate about the first rotational axis, and engaged with the drive gear and coupled to the sample plate such that rotation of the drive gear causes the driven gear and sample plate to rotate.

Preferably, the first rotational axis does not intersect the second rotational axis.

Preferably, the drive gear and driven gears form a hypoid gear arrangement, a SPIRADRIVE™ gear arrangement, or a worm gear arrangement.

According to a second aspect of the present invention there is provided a method of manufacturing a cryostat, the cryostat comprising a rotatable mounting arranged to rotate about the first rotational axis, the mounting extending substantially in a first plane; a sample plate arranged in use to support a sample, located on the rotatable mounting; and a heat sink located adjacent the side of the mounting distant from the sample plate, the method comprising connecting a thermal conductor between the sample plate and the heat sink, such that the conductor extends through an aperture in the rotatable mounting.

According to a third aspect of the present invention there is provided a rotatable sample holder for a cryostat comprising: a sample plate having a first side arranged in use to support a sample; a drive gear arranged to rotate about a first rotational axis; a driven gear arranged to rotate about a second rotational axis, engaged with the drive gear and attached to the sample plate such that rotation of the drive gear causes the driven gear and sample holder to rotate, wherein the first rotational axis does not intersect the second rotational axis.

Preferably, the drive and driven gears form a hypoid gear arrangement.

Preferably, the driven gear forms an integral portion of the sample plate.

Preferably, the driven gear defines an annulus extending in a plane adjacent to the sample plate, on a second side distant from said first.

Preferably, the drive gear is arranged to engage with the driven gear on one side of the sample plate.

The drive and driven gears may form a SPIRADRIVE™ gear arrangement.

Alternatively, the drive and driven gears may form a worm gear arrangement.

Preferably, the drive gear comprises a helical gear, and the driven gear is attached to or is integral with a second side of the sample holder, and comprises a worm wheel.

Preferably, the gear ratio between the first and second gears is greater than 5:1.

According to a fourth aspect of the present invention there is provided a method of manufacturing a rotatable sample holder for a cryostat, the method comprising: providing a sample plate having a first side arranged in use to support a sample; providing a drive gear arranged to rotate about a first rotational axis; providing a driven gear arranged to rotate about a second rotational axis, engaged with the drive gear and attached to the sample plate such that rotation of the drive gear causes the driven gear and sample holder to rotate, such that the first rotational axis does not intersect the second rotational axis.

All of the features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE DRAWINGS

For a better understanding of the invention, and to show how embodiments of the same may be carried into effect, reference will now be made, by way of example, to the accompanying diagrammatic drawings, in which:—

DETAILED DESCRIPTION

Figure 1:
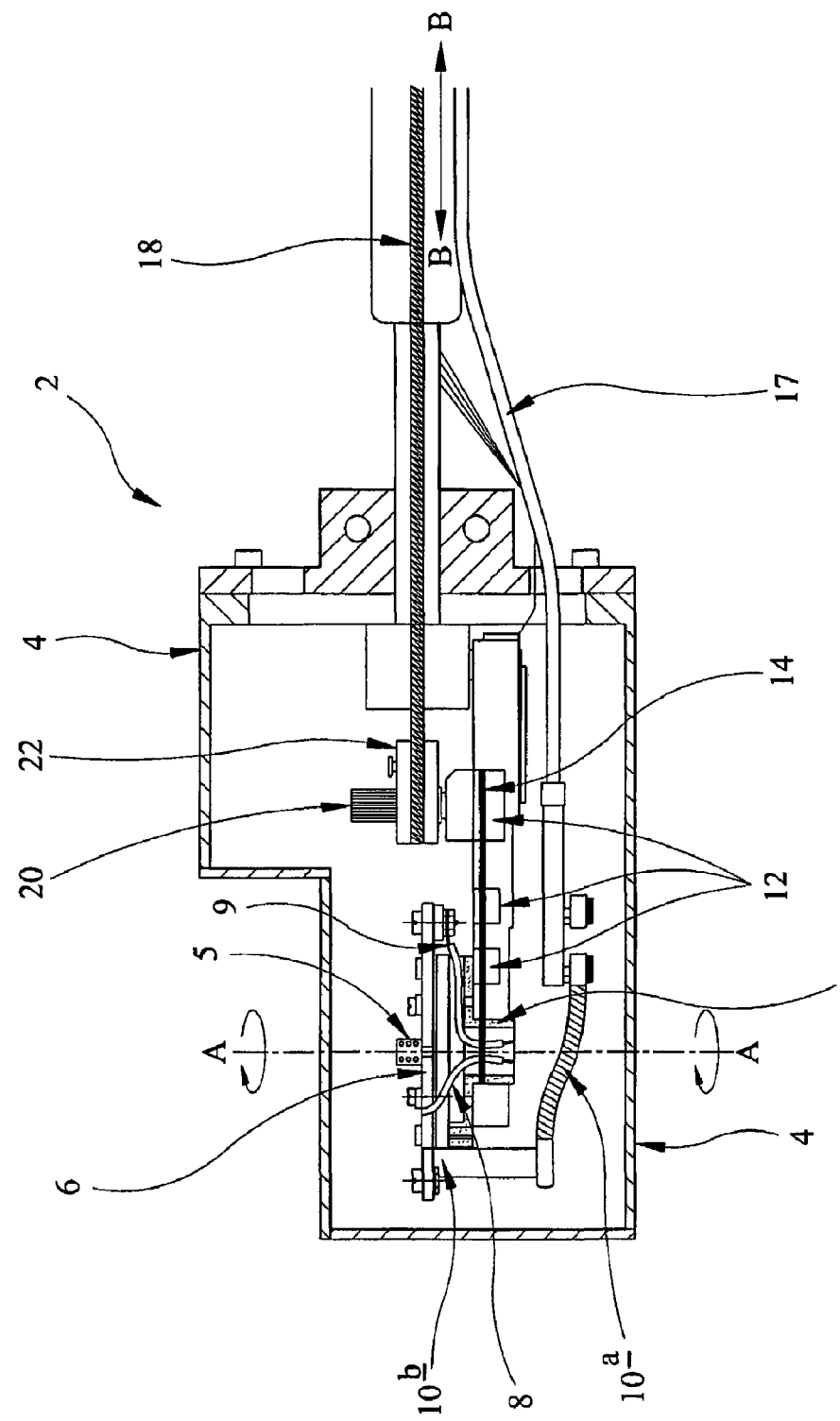
FIG. 1 shows a schematic side view of a prior art cryostat.
Figure 2:
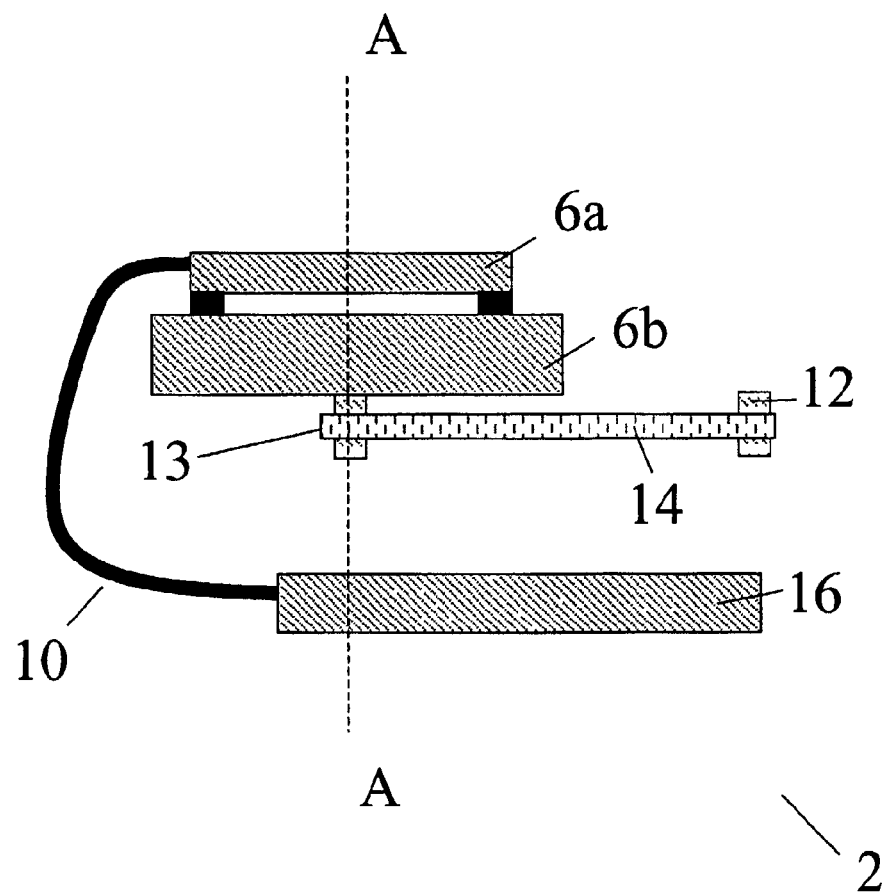
FIG. 2 shows a simplified cross-sectional view of the cryostat shown in FIG. 1.

Referring to FIGS. 1 and 2, there is shown a known cryostat 2. As can be seen from FIG. 1, the cryostat 2 consists of an outer radiation shroud 4 enclosing a sample plate 6 and associated apparatus. In use, a sample 5 is placed on the sample plate 6 and may be securely located on the sample holder by spring clips or clamps. The sample 5 is cooled down to an appropriate temperature in the cryostat 2 by boiling a low temperature liquid into gas, for example, nitrogen or helium. Liquid helium is provided via a first conduit 17 to a helium tank 16 where it is temporarily stored, and then boiled. Gaseous helium leaves the tank 16 via a second conduit 17. The helium tank 16 is thermally coupled with the underside of the sample plate 6 via a flexible copper braid 10a and a cold finger (a rigid thermal conductor) 10b, which contacts the sample plate 6. The sample plate 6 is provided with heater wires 9 and temperature sensor wires 8 connected to opposite edges of the sample plate 6 to heat and monitor the temperature thereof, and therefore the sample 5 positioned thereon. In FIG. 2, the sample plate 6 is shown as two separate components—a sample plate 6a and a rotatable mounting 6b, to reflect some prior art designs in which the mounting is not an integral portion of the sample plate.

Typically, such prior art cryostats 2 can achieve and maintain a temperature of approximately 60K using liquid helium as a cryogen, or approximately 120K using liquid nitrogen.

The sample plate 6 and, hence the sample 5, can be rotated either clockwise or anticlockwise about rotational axis A-A, as shown in FIG. 1. Rotation of the sample plate 6 is achieved by a drive belt 14, which passes over a series of pulleys 12,13 that are positioned underneath the sample plate 6. The final pulley 13, which drives the sample plate 6 is located directly on the rotational axis A-A. The result of this is that the cold finger 10b and copper braid 10a, have to be positioned to the sides of the sample plate 6, away from the rotational axis A-A. A drive shaft 18 reciprocates along axis B-B with one end of the reciprocating drive shaft 18 being attached to a rack 22. The rack 22 turns a pinion 20. The pinion 20/rack 22 arrangement, causes the nearest pulley 12 to rotate. Typically, the drive shaft 18 is turned manually by a user, with one end of the shaft 18 extending to the top of the cryostat, where it is connected to a linear drive mechanism. The drive belt 14 extending around the drive pulley 12 causes the other pulleys 12 to rotate, including the drive pulley 13 directly underneath (and coupled to) the sample plate 6. This causes the sample plate 6 and sample 5 thereon to rotate about axis A-A.

The present inventors have realised that one of the problems associated with known cryostats is that because the drive shaft used to rotate the sample plate is positioned along the rotational axis of sample plate, the cooling conductor 10, consisting in the above example of the copper braid and cooling finger, has to extend around the outside of the mounting of the sample plate and is connected to one side thereof. Hence, there is a relatively long distance between the cooling gas tank and the sample plate between which thermal conduction has to occur for cooling to take place. In addition, conduction has to occur from one side of the sample holder to the opposite side, creating a temperature gradient along the sample plate. This reduces the cooling efficiency of the cryostat. In addition, having the thermal conductor extending around the outside of the sample plate often results in associated leads and cables becoming entangled with each other, which can have a detrimental effect on the manoeuvrability of the sample plate. It also results in a relatively large swept volume, so that any radiation shroud must be large enough to accommodate this volume.

Figure 3:
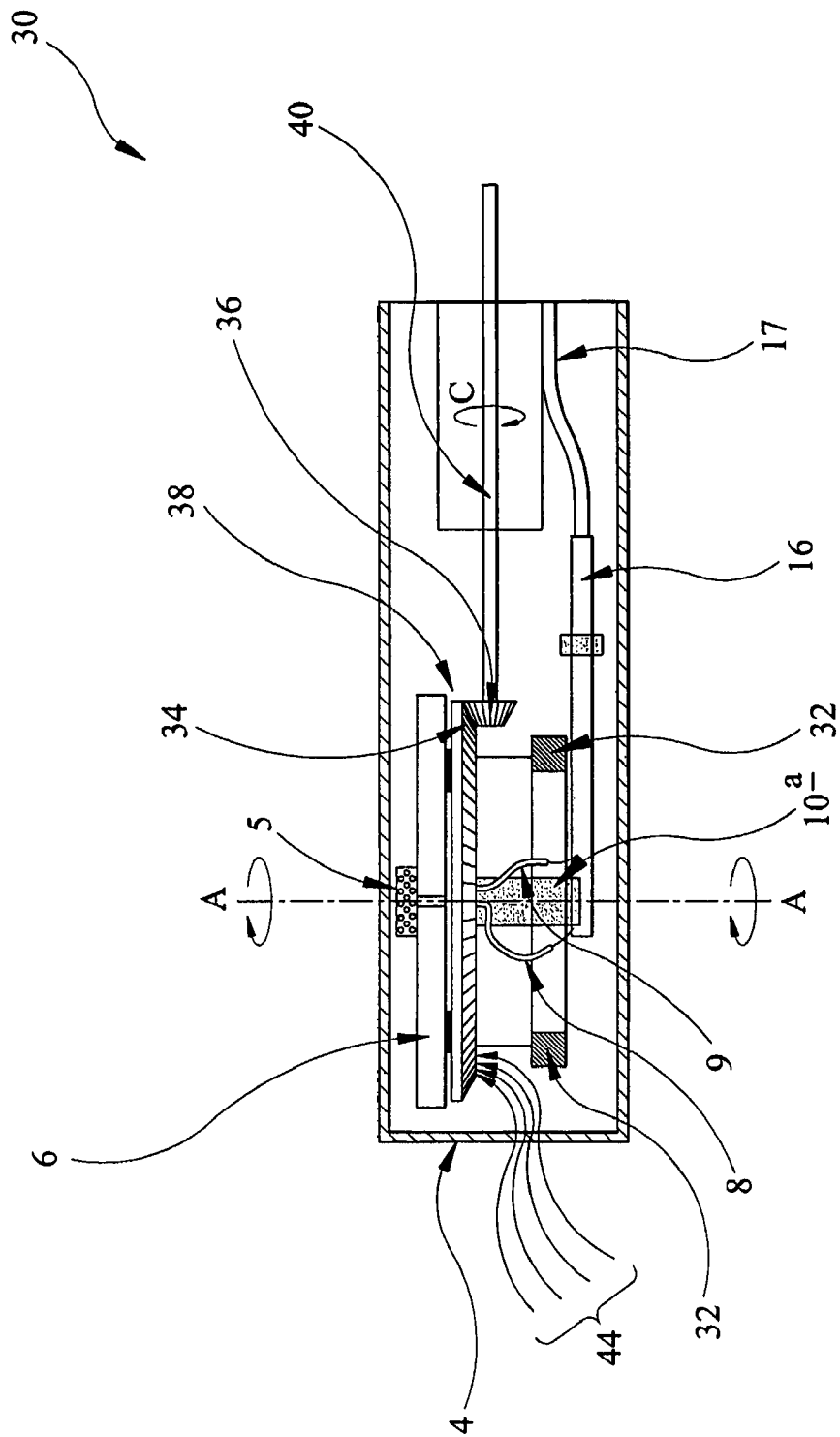
FIG. 3 shows a schematic side view of a cryostat in accordance with an embodiment of the present invention.
Figure 4:
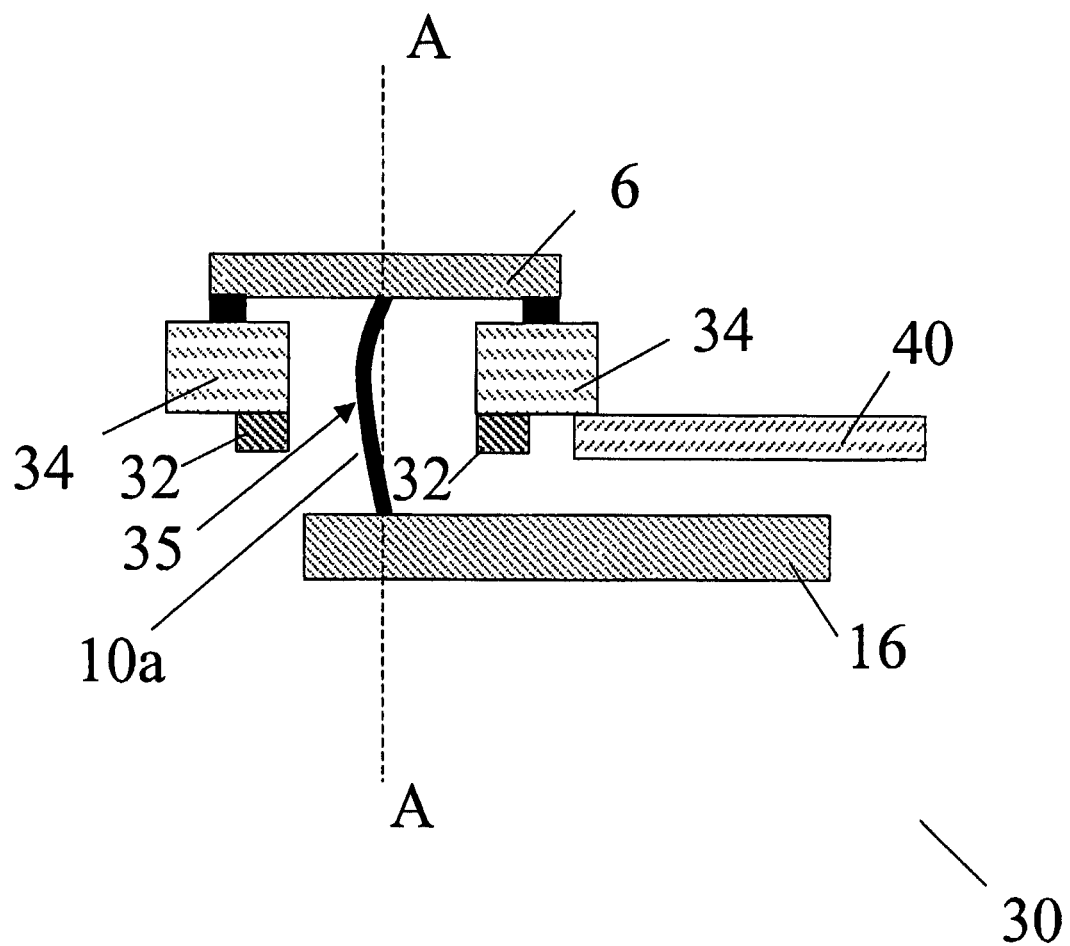
FIG. 4 shows a simplified cross-sectional view of the cryostat shown in FIG. 3.

Referring to FIGS. 3 and 4, there is shown an embodiment of the cryostat 30 of the present invention. Identical reference numerals are used in FIGS. 3 and 4 to represent the same features as those shown in FIGS. 1 and 2. The cryostat 30 consists of a sample plate 6 upon which a sample 5 is placed. The sample plate 6 is mounted on the driven gear 34. The driven gear 34 is supported by a bearing 32. The bearing 32 supports the driven gear 34 from the main body of the cryostat. Both the driven gear 34 and the hollow bearing 32 are annular in shape and mounted about a common axis of rotation A-A. The cryostat further consists of a helium conduit 17, which supplies liquid helium to a helium tank 16, where it boils. The helium tank 16 is thermally connected to the sample plate 6 by a copper braid 10a, which extends through the bearing 32 and an aperture 35 in the driven gear 34. Preferably, the hollow bearing 32 has a relatively large internal diameter (e.g. greater than 5 mm, more preferably greater than 10 mm) so as to prevent the copper braid 10a touching the bearing. Preferably, the aperture 35 through the driven gear 34 is of a similar size. The bearing may be a thin section bearing, and is preferably a full complement bearing. The copper braid 10a is situated on the rotational axis of the sample plate 6. Preferably, the copper braid 10a is connected to the centre of the surface of the sample plate 6 adjacent to the helium tank 16.

The sample plate 6 is also provided with heater wires 9 and temperature sensor wires 8, which extend through the bearing 32 and aperture 35 in the driven gear. The sample plate 6 and cooling connections 10 may all be enclosed within a radiation shroud 4.

In contrast to the drive system used in the prior art cryostat 2, which uses a drive belt 14 on a system of pulleys 12,13, rotation of the sample plate 6 of the cryostat 30 in this embodiment of the present invention, is by means of a hypoid gear set 38. The hypoid gear set 38 consists of a rotating shaft 40 having a drive gear 36 or drive pinion 36 at one end thereof. The drive gear 36 engages with, and drives a driven gear 34, which is attached to the underside of the sample plate 6. The shaft 40 and, hence, drive gear 36 can be rotated in a direction as indicated by arrow C in FIG. 3. Engagement of the drive gear 36 with the driven gear 34 causes the sample plate 6 to rotate about axis A-A. It will be appreciated that the drive gear 36 could be rotated in the opposite direction causing the sample plate 6 to rotate in the opposite direction.

It should be noted that the driven gear is attached to the sample plate, such that rotation of the drive gear causes the driven gear and sample holder to rotate. By attaching the driven gear directly to the sample plate (as opposed to an intervening gear arrangement), any play within the system is reduced, such that the accuracy of movement is improved. In a preferred embodiment, the driven gear forms an integral portion of the sample plate i.e. the driven gear and the sample plate are formed as a single unit.

Figure 6:
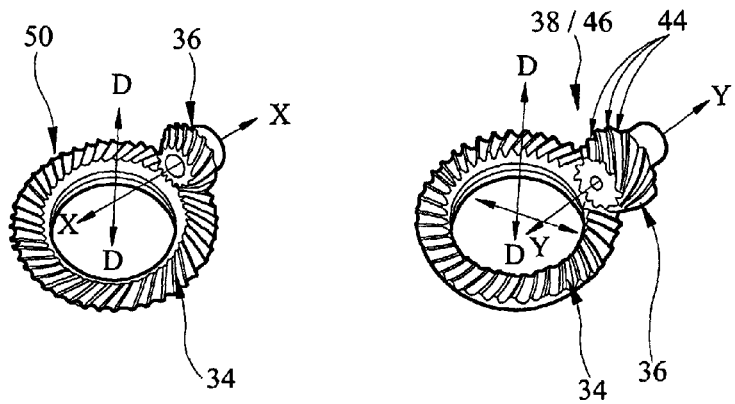
FIG. 6 shows schematic perspective views of a bevel gear, a hypoid gear, and a worm gear.
Figure 6:
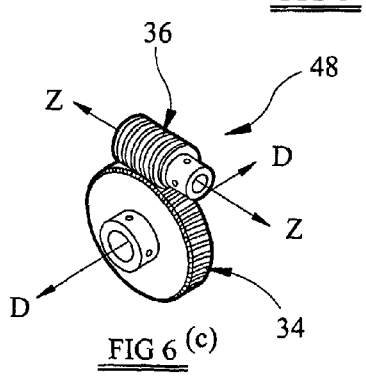

Referring to FIG. 6b, the hypoid gear set 38 is shown in more detail but with the sample plate 6 being removed for clarity. The drive gear 36 consists of a frustoconically shaped head that has one or more spiral teeth and grooves 44 forming a mesh arranged around the outer surface thereof. The teeth and grooves 44 of the drive gear 36 head engage and mesh with teeth and grooves 44 arranged around the surface of the driven gear 34.

The engagement of both sets of teeth/grooves 44 on the drive gear 36 and driven gear 34, ensures accurate control of the driven gear 34. The hypoid gear 38 may have a large gear ratio, for example a ratio of 60:1, such that 60 turns of the drive shaft 40 results in only one rotation of the sample plate 6. This gearing allows very precise rotation of the sample plate 6, and hence, very accurate positioning of the sample 5 thereon. The gear ratio is preferably greater than 25:1, more preferably 50:1, or greater or 60:1 or greater. The drive shaft 40 is coupled via flexible shaft couplings directly to the drive mechanism with no further gear interfaces. This combined with the hypoid gear's inherently low backlash drastically reduces play in the drive system.

Further, as the thermal conductor 10 connecting the tank 16 (i.e. heat sink) and sample plate 6 extends through the aperture 35, the length of the thermal conductor can be decreased compared with prior art designs. This improves the performance of the device, by allowing the sample plate to be cooled to a lower temperature, and to be cooled more quickly. For instance, this allows a cryostat employing such a design to be cooled down to temperatures of less than 20K. Preferably, the thermal conductor is less than 6 cm in length, and more preferably is 5 cm or less, or 3 cm or less, or even 1.5 cm or less.

Preferably, the thermal conductor is connected to a surface of the sample plate within 2 cm of the centre of the sample plate surface, and more preferably within 1 cm of the centre of the sample plate.

Advantageously, having the conductor and/or temperature sensing means positioned along the rotational axis of the rotatable mounting, and connected to the underside of the sample plate, means that associated wires and cables are less likely to become entangled with each other. In addition, the distance between the sample plate and the cooling gas tank in which the cooling gas is boiled is reduced, and this improves the cooling efficacy of the cryostat. Preferably, the thermal conductor is connected adjacent to the centre of the surface of the sample plate.

Although in the above embodiment the thermal conductor extending between the sample plate and the heat sink has been described as a copper braid, it would be appreciated that any thermally conductive element can be utilised. Preferably, the thermal conductor is flexible, and preferably it is formed of a material having a relatively high thermal conductivity, such as copper. Preferably, the thermal conductivity of the material is relatively high at very low temperature (e.g. less than −150° C.), and more preferably the thermal conductivity is greater than 1 W/cmK, and even more preferably it is 10 W/cmK or greater.

In the above embodiment, it has been assumed that the temperature sensor is a thermocouple. A thermocouple is a device consisting of two wires of different metals joined at one end to form a "measuring junction" and connected at their other ends to either a measuring instrument via a "cold junction" or a measuring instrument with cold junction compensation. When a temperature difference between the "measuring junction" and either the "cold junction" or the measuring instrument occurs, an electromotive force (emf) is generated along the wires; this emf can be measured and converted into a temperature reading. However, it will be appreciated that other temperature sensors may be used to monitor the temperature of the cryostat, including the sample plate. In such instances, the temperature sensor will typically also comprise electrical wires. For instance, the temperature sensor could take the form of a resistor, the resistance of which changes with temperature. Four wires are typically connected to such a resistor. Two of the four wires are typically used to pass a small current through the resistor, with the other two wires being used to allow the measurement of the potential difference across the resistor. Similarly, a four wire system can be used with a diode (e.g. a silicon diode), the "forward voltage" of which changes with temperature.

Advantageously, because the rotational axes of the drive gear and driven gears do not intersect, the drive gear is arranged so that it is 'offset' with respect to the driven gear. Having an offset drive gear allows a lower profile in the direction of the axis of the driven gear as it allows support of the sample holder/rotatable mounting to be next to the drive gear rather than above or below it. This simplifies and improves the design of cryostat, which means lower temperatures can be reached. Furthermore, such a sample holder has a more controlled method of manipulation, and this improves the accuracy with which a sample on the sample plate can be manipulated, thereby improving the accuracy of the experiments carried out in the cryostat.

The drive and driven gears may comprise a hypoid gear arrangement. Preferably, the drive gear comprises a shaft having a drive pinion at one end thereof, which shaft and drive pinion are arranged to rotate about the first rotational axis. Preferably, rotation of the shaft and pinion is powered by drive means, for example, a motor. The drive pinion may be of either a parallel or tapered screw form, and may be frusto-conical in shape.

Preferably, the driven gear is attached to or is integral with an underside of the sample plate. The driven gear may define an annulus substantially underneath the sample plate. Preferably, the driven gear comprises a plurality of teeth and grooves, which teeth are suitably sized to mesh with the teeth on the drive pinion.

Preferably, the drive gear is arranged to engage with the driven gear on one side of the sample plate. Hence, the rotational axis of the driven gear defines a straight line that extends through the centre thereof, and that extends substantially perpendicularly away from a plane of the driven gear. The rotational axis of the drive gear defines a straight line that extends substantially parallel with the plane of the driven gear, and that extends off the centre (zero) line thereof. Preferably, the distance between the centre (zero) line of the driven gear and the rotational axis of the drive gear is 10 mm or greater.

Alternatively, the drive and driven gears may comprise a SPIRADRIVE™ gear arrangement. The SPIRADRIVE™ gearing is a proprietary name for a gearset design similar to a hypoid gear arrangement described above, except that it may include an optional straddle extending away from the drive gear pinion substantially along the rotational axis thereof. Preferably, the driven gear comprises a plurality of teeth and grooves, which teeth are suitably sized to mesh with the teeth on the drive pinion. The drive gear may be arranged to engage with the driven gear on one side of the sample plate, i.e. off the zero line of the driven gear.

The drive and driven gears may comprise a worm gear arrangement. Preferably, the drive gear comprises a helical gear, i.e. a shaft having a helical gearing, which shaft is preferably adapted to rotate about the first axis.

Preferably, the driven gear is attached to or is integral with an underside of the sample plate, and may comprise a worm wheel. Preferably, the driven gear comprises a plurality of teeth and grooves extending around the circumference of the worm wheel, which teeth are suitably sized to mesh with the teeth on the helical gear.

Preferably, the drive gear is arranged to engage with the driven gear. Hence, the rotational axis of the driven gear defines a straight line that extends through the centre thereof, and that extends substantially perpendicularly away from a plane thereof. The rotational axis of the drive gear defines a straight line that extends substantially parallel with the plane of the driven gear, and along a tangent from the circumference of the driven gear.

The rotational axis of the drive gear does not intersect the rotational axis of the driven gear, i.e. they are non-parallel, non-intersecting axis gears. The drive and driven gears are adapted to rotate in either a clockwise or an anti-clockwise direction.

Advantageously, the non-parallel, non-intersecting axis gear arrangement in the cryostat, allows very accurate control of the rotation of the sample plate, and hence, position of the sample thereon. This is possible because high gear ratios are achievable, which are substantially higher than is possible when using prior art straight, spiral or zerol bevel gear systems.

Preferably, the drive gear has fewer teeth than the driven gear. Suitably, the gear ratio between the first and second gears is greater than 5:1, more suitably greater than 10:1 and still more suitably greater than 20:1. It is preferred that the gear ratio is greater than 30:1, more preferably, greater than 40:1. However, it is possible that even higher gear ratios may be used, for example, in excess of 100:1, 150:1, 200:1, 250:1, and in excess of 300:1. Use of the gearing means that there is little free play within the mechanism, such that the sample holder can be very accurately controlled.

Figure 5:
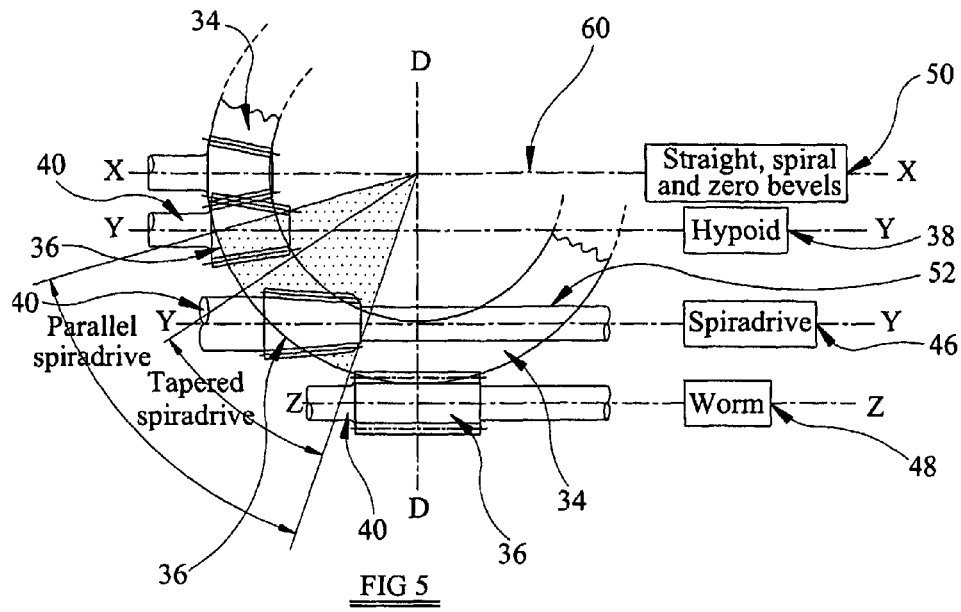
FIG. 5 shows a partial cross-sectional plan view of various types of gearing.

Referring to FIG. 5, there is shown a section of the circumference of the driven gear 34, which would be attached to the underside of the sample plate 6 (which is not shown in FIG. 5 for clarity), and the relationship of a number of different types of drive gears 36 with respect to the driven gear 34. The relationship of each of the different drive gears 36 is shown in more detail in FIGS. 6a-6c. For clarity, the driven gear 34 is shown inverted, and the sample plate 6 is not shown in any of FIGS. 6a-6c. In FIG. 5 and FIG. 6a-6c, the axis of rotation of the driven gear 34 is shown as D-D.

The gearing shown at the top of FIG. 5 and in more detail in FIG. 6a, shows the relationship of straight, spiral and zerol bevel gears 50 with respect to the driven gear 34. The present invention does not extend to bevel gearings; they are merely illustrated and described herein by way of comparison with gearings in accordance with embodiments of the invention. FIG. 5 and FIG. 6a show that the axis of rotation 'X-X' of the drive gear 36 for straight, spiral and zerol bevels extends along the "zero line" of the driven gear 34, i.e. it is radial with respect to the driven gear 34. As shown most clearly in FIG. 6a, the axis of rotation 'X-X' of the drive gear 36 intersects the axis of rotation 'D-D' of the driven gear 34. Hence, bevel gearings 50 are called "intersecting axis gears".

Problems associated with such prior art bevel gearings and rack and pinion gearings used to drive sample plates 6, are that it is not always possible to achieve very high gear ratios, which means a low accuracy of rotation of the driven gear 34, and hence sample plate 6. Furthermore, the intersecting axes of the drive gear 36 and driven gears 34 as shown in FIG. 6a, means that the drive gear 36 has to be directly below the sample plate 6 so that it engages with the driven gear 34. In addition, torque on the driven gear 34 occasionally causes the driven gear 34 to turn the drive gear 36, at least partially, and this decreases the accuracy with which the sample plate 6, and therefore, the sample 5 can be rotationally positioned.

The gearing shown in FIG. 5 directly underneath the bevel gear 50, and in more detail in FIG. 6b, shows the relationship of a hypoid gear 38 in accordance with an embodiment of the invention, with respect to the driven gear 34. FIG. 5 and FIG. 6b show that the axis of rotation 'Y-Y' of the drive gear 36 for the hypoid gear 38, extends in a direction away from, or off, the zero line 60 of the driven gear 34. Hence, as shown most clearly in FIG. 6b, the axis of rotation 'Y-Y' of the drive gear 36 does not intersect the axis of rotation 'D-D' of the driven gear 34. Hence, hypoid gearings 38 are called "non-parallel, non-intersecting axis gears".

The gearing shown in FIG. 5 directly underneath the hypoid gear 38, and also illustrated in FIG. 6b, shows the relationship of a SPIRADRIVE™ gear 46 in accordance with an embodiment of the invention, with respect to the driven gear 34. The SPIRADRIVE™ gear 46 is very similar to the hypoid gear 38, except that it includes an optional straddle 52 extending away from the drive gear head 36. As with the hypoid gear 38, the axis of rotation 'Y-Y' of the SPIRADRIVE™ drive gear 36 does not intersect the axis of rotation 'D-D' of the driven gear 34. The drive gear 36 has fewer teeth 44 than the driven gear 44, and it will be appreciated that the drive gear 36 can be of either a parallel or tapered screw form. The SPIRADRIVE™ gear 46 is a face type similar in appearance to hypoid-offset spiral bevel, and gearing ratios from approximately 6:1 to 360:1 plus (depending upon size) can be achieved. In addition, the mounting requirements of a SPIRADRIVE™ gear 46 are not as critical as a bevel gear 50. Furthermore, since a SPIRADRIVE™ gear 46 has 10-12% of its teeth 44 in continuous mesh, the high contact ratio results in enhancement of strength and smoothness of tooth action within a minimum overall envelope size.

The gearing shown in FIG. 5 underneath the SPIRADRIVE™ gear 46, and also in more detail in FIG. 6c, shows the relationship of a worm gear 48 in accordance with the invention, with respect to the driven gear 34. FIG. 5 and FIG. 6c show that the axis of rotation 'Z-Z' of the drive gear 36 for the worm gear 48, extends in a direction off the zero line 60 of the driven gear 34. Hence, as shown most clearly in FIG. 6c, the axis of rotation 'Z-Z' of the drive gear 36 of the worm does not intersect the axis of rotation 'D-D' of the driven gear 34. Hence, worm gearings are known as "non-intersecting axis gears".

The skilled technician will appreciate that each gear set 38, 46, 48, can be specifically designed for the style and size of cryostat 30 in which it is to be used. Specifically designed gearings can make use of the high ratio possibilities, predictable efficiency options and a choice of suitable materials for use in the cryostat 30 to optimise cost at the required high performance level. For example, the drive gear 36 and driven gear 34 can be made of high strength hardened steels or other alloys. If it is desirable to minimise magnetic fields, the gears can be made of stainless steels, bronzes or other alloys such as beryllium copper.

Advantages of the cryostat 30 reside in the accurate control of the rotation of the sample plate 6. This is made possible by the fact that the rotational axis of the drive gear 36 does not intersect the rotational axis of the driven gear 34. This is the case when either a hypoid gearing 38, SPIRADRIVE™ 46 or worm gearing 48 is used to rotate the sample plate 6. The new drive system has completely dispensed with the drive belt 14 which induced slack in to the prior art system shown in FIG. 1. Hence, the new cryostat 30 can be controlled far more accurately than the prior art cryostat 2.

Use of non-intersecting axis gears (e.g. the hypoid gear 38, SPIRADRIVE™ 46, or worm gearing 48), consisting of the drive gear 36 which engages with the driven gear 34 to one side of the sample plate 6 allows the temperature sensor wires 8 and the cooling connections 10 to be placed at the centre of the underside of the sample plate 6. Hence, they are unlikely to become entangled with each other. Furthermore, use of the hypoid gear 38 means that there is very little free play within the mechanism, such that the sample plate 6 can be very accurately controlled. Although the above sample holder/gear arrangement has been described in conjunction with a sample holder for a cryostat, it will be appreciated that the non-axial gear arrangement could be utilised for any rotatable sample holder arrangement e.g. an environment requiring rotation of the sample holder controlled from a distance from the sample e.g. an experiment on a synchrotron beam line.

In addition, the drive mechanism of the cryostat 30 is not bulky as with prior art cryostats 2, because the pulley system 12 is not required, which means that a smaller radiation shroud 4 may be used to enclose the apparatus making the apparatus more versatile and cheaper to manufacture. Furthermore, because the equipment is not bulky, there is less surface area to absorb radiation, and so it is possible to achieve lower temperatures with the present invention. For example, temperatures obtained with the new cryostat are as low as 10 Kelvin using liquid helium.

The invention claimed is:

1. A cryostat comprising:
    a rotatable mounting arranged to rotate about a first rotational axis, the rotatable mounting defining an aperture that surrounds the first rotational axis;
    a sample plate having a surface that is arranged in use to support a sample, the sample plate located on the rotatable mounting and the surface extending substantially perpendicular to the first rotational axis, the sample plate at least partially covering the aperture of the rotatable mounting;
    a cryogenic tank containing cryogenic material and located adjacent a side of the rotatable mounting distant from the sample plate; and
    a thermal conductor extending between the sample plate and the cryogenic tank, wherein the conductor extends through the aperture in the rotatable mounting.

2. A cryostat according to claim 1, wherein the thermal conductor comprises a flexible cable extending through the aperture.

3. A cryostat according to claim 2, wherein said flexible cable comprises copper braid.

4. A cryostat according to claim 1, wherein the rotatable mounting is substantially annular, and the aperture extends substantially through the centre thereof.

5. A cryostat according to claim 1, wherein at least a portion of the thermal conductor is substantially collinear with said first rotational axis.

6. A cryostat according to claim 1, wherein the thermal conductor does not contact the rotatable mounting.

7. A cryostat according to claim 1, wherein the thermal conductor is less than 5 cm in length.

8. A cryostat according to claim 1, wherein the cryostat comprises a temperature sensor comprising electrical wires, the electrical wires extending through the aperture.

9. A cryostat according to claim 8, wherein at least one of the thermal conductor and the temperature sensor is connected to a side of the sample plate adjacent the cryogenic tank.

10. A cryostat according to claim 1, further comprising a hollow bearing extending around said first rotational axis, the thermal conductor extending through the bearing, and the bearing supporting the rotatable mounting.

11. A cryostat according to claim 1, wherein the cryostat further comprises a drive gear arranged to rotate about a second rotational axis, the rotatable mounting comprising a driven gear arranged to rotate about the first rotational axis, and engaged with the drive gear and coupled to the sample plate such that rotation of the drive gear causes the driven gear and sample plate to rotate.

12. A cryostat according to claim 11, wherein the first rotational axis does not intersect the second rotational axis.

13. A cryostat according to claim 11, wherein the drive gear and driven gear form one of a hypoid gear arrangement, a SPIRADRIVE™ gear arrangement, or a worm gear arrangement.

14. The cryostat according to claim 1, wherein the thermal conductor contacts a center of the sample plate.

15. The cryostat according to claim 14, wherein the first rotational axis extends through the center of the sample plate.

16. The cryostat according to claim 1, wherein the thermal conductor includes first and second opposite ends; wherein the first end of the thermal conductor is directly attached to the portion of the sample plate that at least partially covers the aperture; wherein the thermal conductor extends through the aperture in the rotatable mounting without contacting the rotatable mounting; and wherein the second end of the thermal conductor is in direct communication with at least one of the cryogenic tank and the cryogenic material.

* * * * *